(12) United States Patent
Lundh et al.

(10) Patent No.: US 11,246,772 B2
(45) Date of Patent: Feb. 15, 2022

(54) BANDAGE SECURING DEVICE (71) Applicant: PRESSCISE AB, Herrljunga (SE)

(72) Inventors: Torbjörn Lundh, Billdal (SE); Jonatan Vasilis, Gothenburg (SE); Josefin Damm, Ljung (SE)

(73) Assignee: PRESSCISE AB, Herrljunga (SE)

( * ) Notice: Subject to any disclaimer, the term of this patent is extended or adjusted under 35 U.S.C. 154(b) by 762 days.

(21) Appl. No.: 15/560,109

(22) PCT Filed: Mar. 24, 2016

(86) PCT No.: PCT/SE2016/050248
§ 371 (c)(1),
(2) Date: Sep. 20, 2017

(87) PCT Pub. No.: WO2016/153421
PCT Pub. Date: Sep. 29, 2016

(65) Prior Publication Data
US 2018/0098897 A1    Apr. 12, 2018

(30) Foreign Application Priority Data
Mar. 25, 2015   (SE) .................................. 1550354-3

(51) Int. Cl.
*A61F 15/00* (2006.01)
*A61F 13/00* (2006.01)

(52) U.S. Cl.
CPC ...... *A61F 15/006* (2013.01); *A61F 13/00085* (2013.01); *A61F 15/005* (2013.01);
(Continued)

(58) Field of Classification Search
CPC ............................ A44B 18/00; Y10T 24/2708
(Continued)

(56) References Cited

U.S. PATENT DOCUMENTS 2,820,456 A    1/1958   Peerless et al.
3,036,572 A    5/1962   Castelli et al.
(Continued)

FOREIGN PATENT DOCUMENTS

EP    0 321 234 A1    6/1989
WO    2011/048171 A1  4/2011
(Continued)

OTHER PUBLICATIONS

International Search Report (PCT/ISA/210) dated May 13, 2016, by the Swedish Patent Office as the International Searching Authority for International Application No. PCT/SE2016/050248.
(Continued)

*Primary Examiner* — Caitlin A Carreiro
(74) *Attorney, Agent, or Firm* — Buchanan Ingersoll & Rooney P.C.

(57)    ABSTRACT

A bandage securing device composed of a first sheet part and a second sheet part, and optionally also a third sheet part. The first and second sheet parts are connected to each other along a connection line extending in a width direction and arranged to overlap each other, thereby forming a jaw-like structure in a longitudinal direction. At least one of the first and second sheet parts, and possibly both, are provided with at least one first adherent fastening layer on an internal surface facing the overlap. Further, the bandage securing device can include at least one second adherent fastening layer on an external surface, not facing the overlap, to detachably connect to the bandage. This second adherent fastening layer may be provided on one of the first and second sheet parts, and/or on the third sheet part.

10 Claims, 4 Drawing Sheets

(52) U.S. Cl.
CPC ............... *A61F 13/00063* (2013.01); *A61F 2013/00127* (2013.01); *A61F 2013/00565* (2013.01)

(58) Field of Classification Search
USPC .... 602/57, 75, 76, 78, 79; 24/578.1, 578.15, 24/584.1, 589.1, 306
See application file for complete search history.

(56) References Cited

U.S. PATENT DOCUMENTS

| | | | |
|---|---|---|---|
| 3,039,461 A | | 6/1962 | Hawie |
| 3,307,233 A | | 3/1967 | Mahlmann et al. |
| 3,373,742 A | | 3/1968 | Shears et al. |
| 3,863,301 A | | 2/1975 | Leveen |
| 3,880,161 A | | 4/1975 | Fossel |
| 4,586,499 A | | 5/1986 | Kaletzky |
| 4,862,563 A | * | 9/1989 | Flynn .................. A44B 18/00 24/442 |
| 4,926,848 A | * | 5/1990 | Shimkus ............. A61F 13/0273 128/DIG. 15 |
| 5,785,011 A | * | 7/1998 | Gitterman, III .......... B68B 1/02 119/865 |
| 2007/0124899 A1 | * | 6/2007 | Israel ................. A44B 18/0084 24/306 |
| 2012/0116278 A1 | | 5/2012 | Donald |
| 2014/0081189 A1 | * | 3/2014 | Ingimundarson ....... A61F 5/028 602/19 |
| 2014/0142533 A1 | | 5/2014 | Peltier et al. |
| 2015/0342803 A1 | | 12/2015 | Julian et al. |

FOREIGN PATENT DOCUMENTS

| | | |
|---|---|---|
| WO | 2012/006103 A2 | 1/2012 |
| WO | WO 2014/093077 A1 | 6/2014 |
| WO | WO 2014/155014 A1 | 10/2014 |

OTHER PUBLICATIONS

Written Opinion (PCT/ISA/237) dated May 13, 2016, by the Swedish Patent Office as the International Searching Authority for International Application No. PCT/SE2016/050248.

Extended European Search Report dated Jul. 13, 2018, issued by the European Patent Office in corresponding European Application No. 16769176.5-1102 (6 pages).

* cited by examiner

BANDAGE SECURING DEVICE

TECHNICAL FIELD OF THE INVENTION

The present invention relates to a bandage securing arranged to detachably connect to a bandage end, as well as a corresponding bandage assembly.

BACKGROUND

A bandage is used to create localized pressure and is commonly used to inhibit or treat an established swelling. Bandages are also used to enhance the venous return in individuals with either venous insufficiency or obstruction. Another application of bandage is to deliver a drug, for example through a dressing applied on the bandage. For non-medical indications, bandages are applied to reduce the risk of muscle sprain and strains and to improve performance and recovery after physical activities.

To make the bandage as comfortable as possible to wear, it is usually made of a soft fabric. Hence, the bandage will typically not stick to itself when wrapped around the body part, and to prevent the bandage from unwrapping, it is necessary to secure the end of the bandage at the final wrap. Most commonly, this is achieved using small metal clips with sharp prongs which pierce the material and fixes the end of the bandage to a previous turn of the bandage. Other methods include adhesive tape, safety pins or hook and loop systems integrated with the bandage.

A traditional and very simple method of securing a bandage is to use small metal clips with sharp prongs, with half of the clip connected to the end of the bandage and the other half to the bandage material of a previous turn. However, as the sharp sharp prongs are close to the skin, there is a risk of injury. Furthermore, the clips are easy to lose in case they fall off or when they are not used. Yet another drawback of the traditional fastening devices is that the material has to be able to withstand, with minimal tearing, large forces in the longitudinal direction of the bandage. This latter problem is particularly pronounced at the end of the bandage, and especially if the length of the bandage has been adjusted at the time of application.

U.S. Pat. No. 2,820,456 discloses a fastening device with hooks that improves upon the traditional clip by pointing the hooks away from the skin and reducing the force on individual hooks by utilizing the full width of the bandage. This design, however, does not eliminate the risk of injury, since the hooks are still exposed. In fact, compared to the traditional clip, there is a greater chance of clothes getting stuck in the hooks.

An improvement in a different direction is found in U.S. Pat. No. 3,036,572, which discloses a bandage with a clip—similar to the traditional clip—already attached to an end of the bandage. By attaching the clip to the bandage the clip cannot be lost, but it also becomes necessary to wrap the bandage around the body part in such a direction that the prongs can attach to the bandage at the final wrap. This drawback is addressed by the attached fastening devices in U.S. Pat. Nos. 3,373,742 and 3,863,301, which disclose clips that can be applied in both orientations. In all three cases, however, the length of the bandage has to be determined beforehand, and the risk with exposed prongs still remains.

U.S. Pat. No. 3,880,161 addresses the risk of injury by replacing the sharp prongs with hook and loop fasteners, again at the price of having to wrap the bandage around the body part in a certain direction. U.S. Pat. No. 4,926,848 discloses a design where the hook and loop surfaces wrap around a transversal section of the bandage, thus allowing the bandage to be fastened regardless of what direction it was wrapped in. Both designs, however, require the length of the bandage to be determined beforehand and, secondly, can be costly to manufacture.

Finally, WO2014/093077A1 discloses a design which combines a buckle, that can mechanically lock the end of the bandage in place, with a strap that can adhere to the bandage material from a previous wrap by the use of for instance adhesives or micro hooks. Such a design essentially eliminates the risk of injury, allows the length of the bandage to be determined at the time of application and, due to its size, reduces the chance of the fastening device getting lost. However, in order to be able the mechanically lock the end of the bandage, the buckle has to be rather sturdy, which makes it less comfortable for the wearer. Furthermore, locking the bandage in place by mechanical means subjects the bandage material to stresses in the normal direction, increasing the risk of tears in the material. Finally, such a design in itself does not prevent the end if the bandage from unravelling.

Hence, there is need for an improved bandage securing device. In particular there is a need for a new bandage securing device that not expose sharp prongs, that is comfortable for the wearer, does not easily get lost, allows for repeated applications and/or prevents the bandage material from unravelling, especially at the end of the bandage.

SUMMARY OF THE INVENTION

There is therefore an object of the present invention to provide a bandage securing device which at least partly alleviates the above-discussed drawbacks, and at least partly addresses the above-identified needs.

This object is achieved by means of a bandage securing device and a bandage assembly in accordance with the appended claims.

According to a first aspect of the invention there is provided a bandage securing device comprising a first sheet part and a second sheet part, wherein the first and second sheet parts are connected to each other along a connection line extending in a width direction and arranged to overlap each other, thereby forming a jaw-like structure in a longitudinal direction, at least one of said first and second sheet parts being provided with at least one first adherent fastening layer on an internal surface facing said overlap, and wherein said bandage securing device further comprises at least one second adherent fastening layer on an external surface, not facing said overlap, said adherent fastening layers being arranged to detachably connect to the bandage.

It has been found by the present inventors that this bandage securing device provides a number of advantages. It is relatively easy and cost-effective to manufacture, and adheres strongly and reliably to most types of known and available bandages. It also adheres without any sharp prongs or other rigid and sharp objects, and can in its entirety be made of a relatively soft and flexible material. This makes the bandage securing device easy to use, and apply, and also very comfortable to wear. Once attached to a bandage, the bandage securing device also remains in place until a deliberate and intentional removal thereof, thereby facilitating application etc. This also alleviates the risk of losing the bandage securing device. The bandage securing device is also cost-efficient to use, since it renders bandage application and fastening quick and controllable, and since the bandage securing device can be reused many times. Still further, the bandage securing device protects the bandage end, thereby prolonging the longevity of the bandage.

The bandage securing device can be manufactured in a soft material, in order to make it feel integrated with the bandage and and comfortable to wear, while still remaining detachable. Furthermore, the jaw-like structure protects at least a portion of the end of the bandage which is most prone to tearing by shielding it from wearing due to external forces. Another benefit of the jaw-like structure is that it allows for a duplication of the surface area of the adherent fastening layers compared to a single sheet, for a given longitudinal length of bandage, which is useful since any fastening device tends to influence the stretching properties, and hence therapeutic effects, of the bandage.

By means of the present invention, the jaw-like structure also allows for the adhesive layers provided on the first sheet part and second sheet part to interact. For instance, if the fabric of the bandage is rather sparse, then a hook-and-loop type of system can be used, with hooks on one of said sheet parts and loops on the other sheet part.

Preferably, both the sheet parts have an extension in a width direction corresponding to at least the greater part of the width of the bandage, and preferably an extension in the width direction being equal to or greater than the width of the bandage. This facilitates provision of a reliable connection between the bandage and the bandage securing device. It also provides a good force distribution in the bandage when using the bandage securing device as a pulling means when applying the bandage. Further, this ensures that a good sealing and protection of the entire bandage end is obtained.

The securing device may further preferably comprise a third sheet part, which is connected to the first and second sheet parts via said connection line, and extending away from said overlap, as seen from said connection line. Hereby, connection to the underlying bandage is facilitated, and a better pulling grip is facilitated. Preferably, at least one of said second adherent fastening layer(s) is arranged on a surface of said third sheet part. The third sheet may also form a gripping handle. For example, the third sheet may be provided with a textured or corrugated surface, for improved grip, be provided with a gripping opening, or the like.

The first and second sheet parts may form a monolithic integrated sheet, said connection line thereby forming a folding line. However, alternatively, the first and second sheet parts may be provided as separate sheet parts, being connected together by means of sewing, welding or the like. In case a third sheet part is provided, this may also be a separate sheet parts, connected to the other sheet parts in a similar way. However, in a preferred embodiment, the third sheet part forms a monolithically integrated part of at least one of said first and second sheet parts.

At least one, and preferably both, of said first and second adherent fastening layers preferably have an extension in the width direction essentially corresponding to the width of the sheet parts on which they are arranged.

The first and second adherent fastening layers preferably each comprises a plurality of hooks, arranged to engage in thread or yarn loops formed in a material of the bandage to form a detachable hook-and-loop connection. It has been found that such a hook-and-loop connection, e.g. realized as a Velcro-type connection, provides a very reliable attachment, at the same time as being easy to detach.

Preferably, both internal surfaces of said first and second sheet parts are provided with said first adherent fastening layers. Hereby, attachment to the bandage end occurs at both sides, which provides an even more reliable connection.

At least one of said first and second sheet parts may be provided with said second adherent fastening layer, on an external surface thereof. Additionally or alternatively, such a second adherent fastening layer may be provided on a third sheet part, on an external surface thereof.

At least one of said sheet parts being provided with an adherent fastening layer may further comprise a non-adherent surface area, not being provided with said adherent layer, and arranged in a part of said sheet part being opposite to said connection line. This provides an easily gripped, non-attached tab area, which facilitates detachment.

The at least one of the first and second sheet parts being provided with the first adherent fastening layer may further comprise a non-adherent surface area, not being provided with said adherent fastening layer, and arranged in a part of said sheet part being closest to said connection line. This makes it possible to adequately secure the bandage, but without attaching to the very end of the bandage. This ensures that the bandage is not damaged during attachment and de-attachment.

According to another aspect of the invention, there is provided a bandage assembly comprising:
 a bandage, formed of an elongate fabric material; and
 a bandage securing device as discussed in the foregoing.

Hereby, similar advantages and specific features as discussed above in relation to the first aspect are obtainable and useable.

The bandage is preferably made of an elastic material, and is woven or knitted from threads or yarns.

These and other aspects of the invention will be apparent from and elucidated with reference to the embodiments described hereinafter.

BRIEF DESCRIPTION OF THE DRAWINGS

For exemplifying purposes, the invention will be described in closer detail in the following with reference to embodiments thereof illustrated in the attached drawings, wherein.

DETAILED DESCRIPTION OF PREFERRED EMBODIMENTS

In the following detailed description, preferred embodiments of the present invention will be described. However, it is to be understood that features of the different embodiments are exchangeable between the embodiments and may be combined in different ways, unless anything else is specifically indicated. It may also be noted that, for the sake of clarity, the dimensions of certain components illustrated in the drawings may differ from the corresponding dimensions in real-life implementations. Even though in the following description, numerous specific details are set forth to provide a more thorough understanding of the present invention, it will be apparent to one skilled in the art that the present invention may be practiced without these specific details. In other instances, well known constructions or functions are not described in detail, so as not to obscure the present invention. Further, the same reference signs are used to designate equal or similar parts throughout the drawings.

Figure 1:
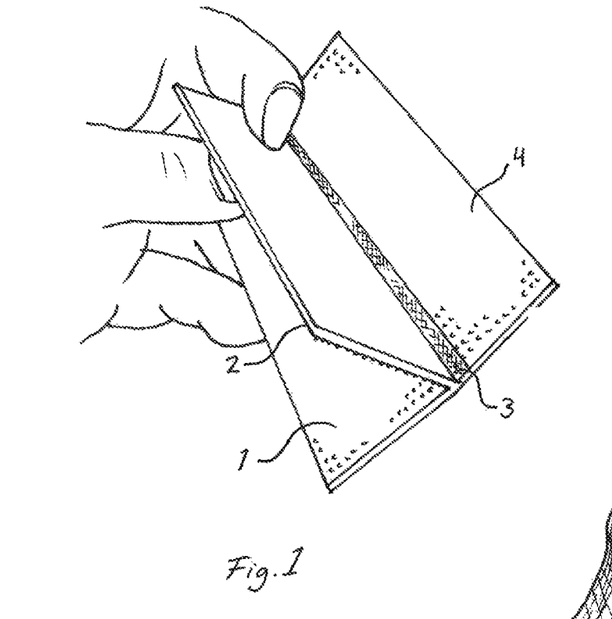
FIGS. 1-3 are perspective views of a bandage securing device in accordance with one embodiment of the invention, illustrating various steps during attachment to a bandage end.

FIG. 1 shows one preferred embodiment of the invention. A first sheet part 1 and a second part 2 are connected to each other along a connection line 3, forming a jaw-like structure, and the two facing surfaces have an adherent fastening layer in the form of hooks in a hook-and-loop-system. A third sheet part 4 is connected to the same connection line 3 and is also provided with an adherent fastening layer, again in the form of hooks. In another embodiment, the adherent fastening layers do not attach to the bandage using hooks, and may for instance instead chemically bond to the bandage material in a detachable way. The adherent fastening layers may also be either of the same type or of different types. Thus, in yet another set of embodiments at least one of the three sheet parts has a different fastening layer than the rest.

Figure 2:
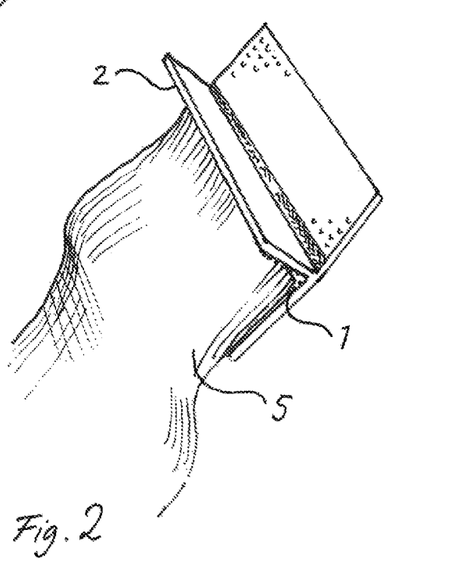
Figure 3:
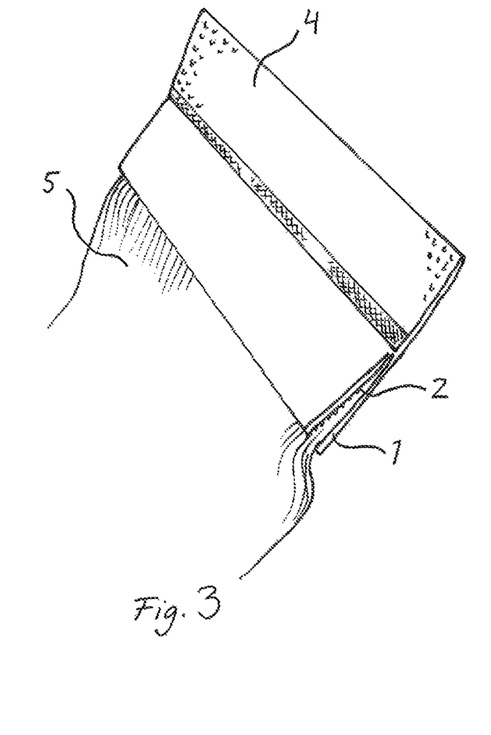

In FIG. 2, the end of the bandage 5 attaches to the first adherent fastening layer of the first sheet part 1, within the jaw-like structure formed by the first and second sheet parts 1 and 2. In FIG. 3, the second sheet part 2 is brought towards the bandage 5 and first sheet part 1, thereby closing the jaw-like structure, and letting the adherent fastening layer of the second sheet part 2 attach to the bandage 5. The jaw-like structure ensures both that the bandage securing devices securely attaches to the bandage and that the end of the bandage is protected from accidental unraveling.

Figure 4:
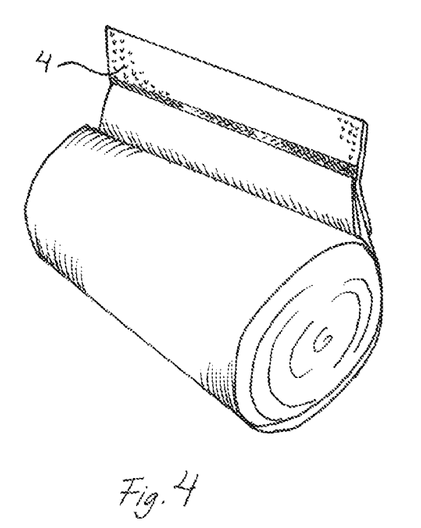
FIGS. 4-5 are perspective views of the bandage securing device of FIGS. 1-3, illustrating the use of the bandage securing device for securing a rolled-up bandage.
Figure 5:
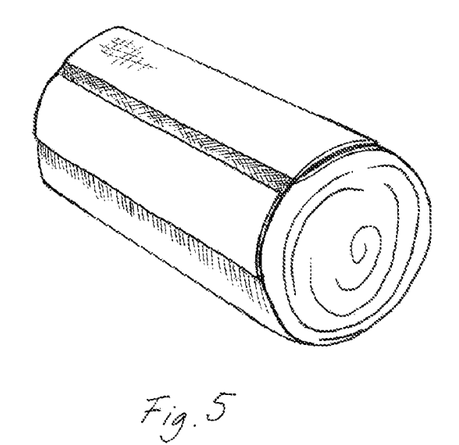

FIG. 4 shows one preferred embodiment of the bandage securing device when attached to the exterior bandage end of a roll of bandage. When the second adherent fastening layer on the third sheet part 4 is brought in contact with the roll of bandage, the roll of bandage is secured, as pictured in FIG. 5. The process of fastening the bandage end is reversible, and the roll of bandage can be secured and unsecured multiple times. As a bandage is usually unrolled gradually when applied to a body part, the bandage securing device is in this case first detached from the bandage by reversing the procedure shown in FIGS. 2 and 3. Having wrapped all but the last few turns of the bandage, which may have been shortened in situ, around a body part the bandage securing device is attached to the bandage end as pictured in FIGS. 2 and 3.

Figure 6:
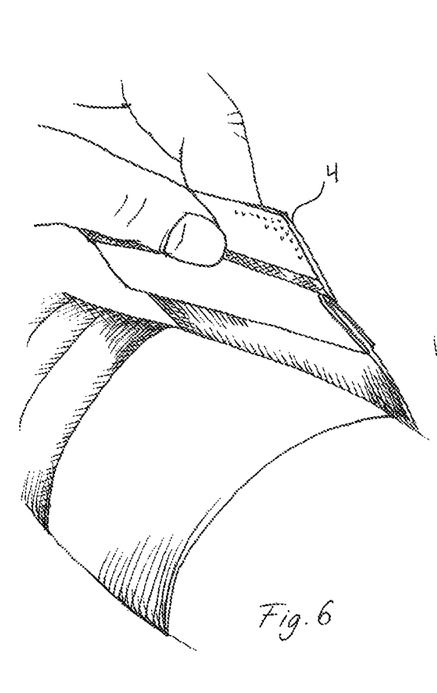
FIGS. 6-7 are perspective views of the bandage securing device of FIGS. 1-3, illustrating the use of the bandage securing device for securing a bandage applied to a user.
Figure 7:
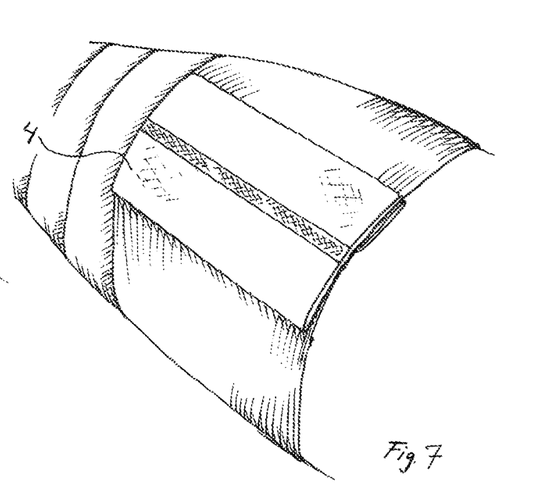

FIG. 6 shows how the third sheet part 4 is used as a handle when the last turn of the bandage is wrapped around a body part. In another embodiment, there is no third sheet part, but it is still possible to utilize the first two sheet parts as a handle. In embodiments where the second adherent fastening layer on a sheet part adheres to the skin, or is otherwise uncomfortable to touch, it is preferred to also provide a non-adherent surface area on the sheet part, which need not be larger than a typical thumbprint, in order to allow for a non-adherent and comfortable grip. In all embodiments, such a handle allows for a more even stretching of the bandage in both the length and width directions of the bandage, which allows for greater forces to be applied without tearing the bandage material. Finally, the second adherent fastening layer is brought in contact with the bandage from previous turns, which secures the bandage to the body part, as seen in FIG. 7.

Figure 8:
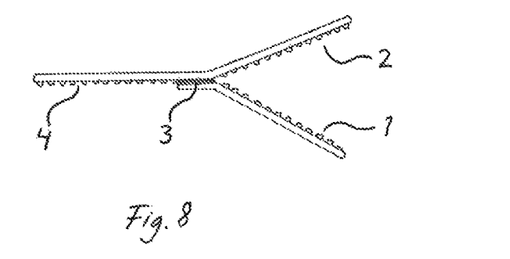
FIGS. 8-16 are side views schematically illustrating various embodiments and realizations of bandage securing devices in accordance with the invention.
Figure 9:
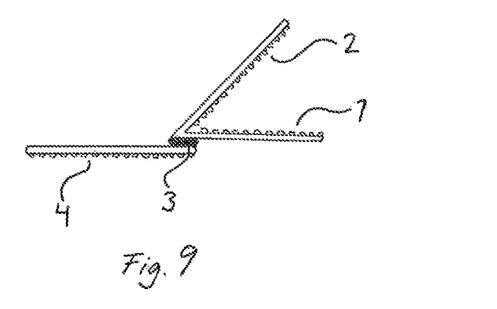

In FIGS. 8 and 9, two possible constructions to construct and join the sheet parts of the embodiment of FIG. 1 are shown. In FIG. 8, the second sheet part 2 and third sheet part 4 form a monolithically integrated part and the first sheet part 1 is attached to said monolithically integrated part along the connection line 3. Conversely, FIG. 9 shows an embodiment where the first sheet part 1 and the second sheet part 2 form a monolithically integrated part which folds along a connection line 3, to which the third sheet part 4 is attached.

Figure 10:
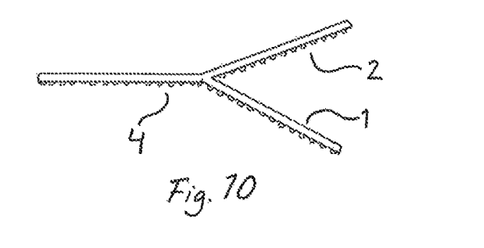

FIG. 10 shows an embodiment where the first adhesive fastening layer is applied only to the second sheet part 2. In the pictured embodiment, the second adhesive fastening layer is also applied to both the first sheet part 1 and the third sheet part 4. One use of such an embodiment is when one wishes to first apply the bandage fastening device to the bandage already applied to the body part and then try various lengths of the last turn of the bandage, which is made easier if the bandage does not immediately come in contact with the first adhesive fastening layer.

Figure 11:
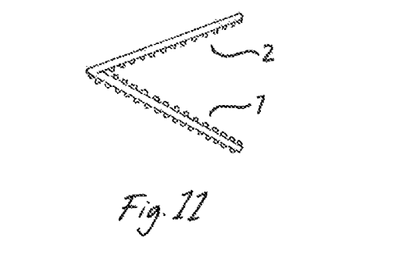

FIG. 11 shows an embodiment having only a first sheet part 1 and a second sheet part 2. The second adhesive layer is here applied to the external surface of the first sheet part 1.

Figure 12:
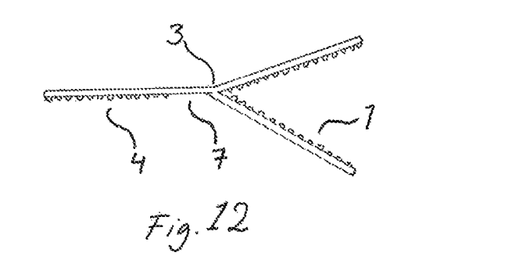
Figure 13:
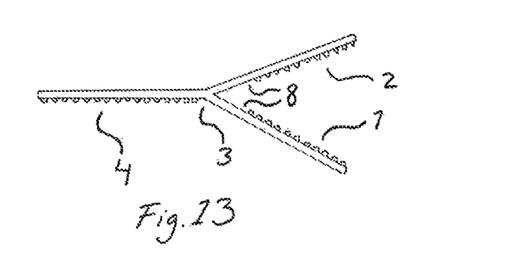

At least one of the sheet parts being provided with an adherent fastening layer may further comprise a non-adherent surface area, not being provided with said adherent layer, and arranged in a part of said sheet part being opposite to said connection line and/or arranged in a part of said sheet part being closest to said connection line. For example, FIG. 12 shows an embodiment with a third sheet part 4, where the second adhesive fastening layer is applied only to a portion of the third sheet part, leaving a section 7 of the sheet part towards the connection line 3, which it may encompass, without an adhesive fastening layer. Such a section is useful from a manufacturing point of view as it allows for finished sheet parts, with adhesive fastening layers already applied, to be fused together using for instance welding. In another embodiment, the second adhesive fastening layer is applied also to the first sheet part 1. As an alternative embodiment, FIG. 13 shows an embodiment where the first adhesive fastening layer is applied to both sheet part 1 and sheet part 2, but leaves a section 8 of the interior surfaces towards the connection line 3 without an adhesive fastening layer. This reduces the risk of the end of the bandage becoming unravelled when the bandage fastening device is attached and detached multiple times.

Figure 14:
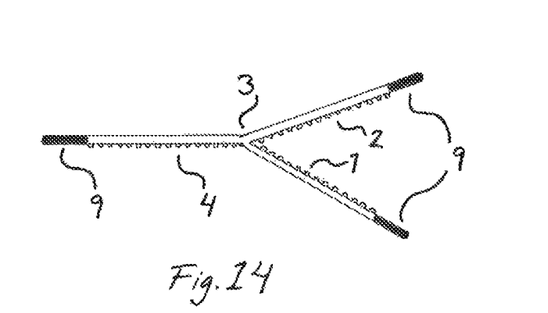

The end of one or several of the sheet parts, in particular when provided with outer non-adherent areas, may function as a gripping handle. For example, FIG. 14 shows an embodiment with three sheet parts, where all sheet parts are equipped with dedicated gripping sections 9 at the ends of the first sheet 1, second sheet part 2 and third sheet part 4 that are away from the connection line 3. Such an embodiment facilitates the detachment of the bandage securing device, both to remove the bandage from the body part and to remove the bandage securing device from the bandage itself. In other embodiments there is a dedicated gripping section 9 only on the third sheet part 4, which may not even be provided with a second adhesive fastening layer, for the case where the primary need is to be able to remove the bandage from the body part. Conversely, there may be a dedicated gripping section 9 only on the first sheet part 1 and second sheet part 2, in order to facilitate the removal of the bandage securing device over the removal of the bandage from the body part. In yet another embodiment, there is a dedicated gripping section 9 only on one of the first and second sheet parts 1 and 2, which still makes it easier to open the jaw-like structure to remove the bandage. In embodiments where only one of the first sheet part 1 and second sheet part 2 has a gripping section 9, it is preferred to place the gripping section on the sheet part that is closest to the body part in order to prevent accidental removal or, in embodiments where the third sheet part 4 also has a gripping section, usage of the wrong gripping section to remove the bandage from the body part.

Figure 15:
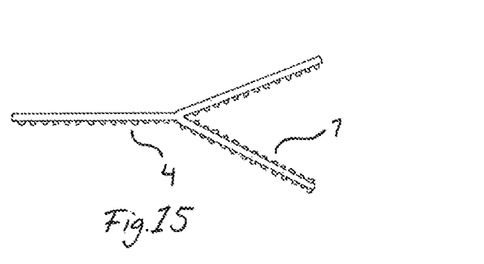

FIG. 15 shows an embodiment where both the first sheet part 1 and the third part 4 are provided with the second adhesive fastening layer.

Figure 16:
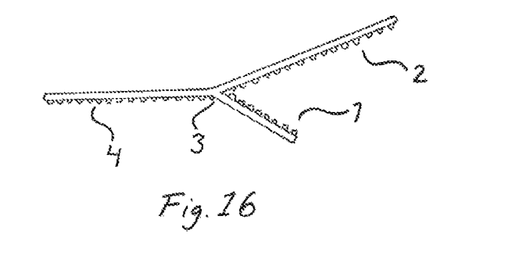

The sheet parts may have varying and different lengths and geometries. As an example, FIG. 16 shows an embodiment where the first sheet part 1 is shorter than second sheet part 2, as measured from the common connection line 3. In another embodiment, the first sheet part 1 is instead longer than the second sheet part 2. In yet another embodiment, the length of the third sheet part 4 varies independently of the lengths of the first sheet part 1 and second sheet part 2.

Figure 17:
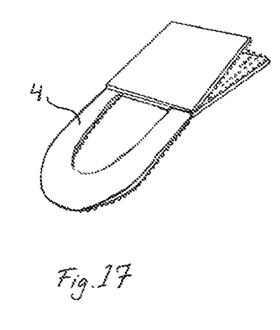
FIGS. 17-19 are perspective views illustrating further embodiments of bandage securing devices in accordance with the invention.

FIG. 17 shows an embodiment where the third sheet part 4 has the shape of a handle. In some embodiments there is a second adhesive fastening layer on the third sheet part. In other embodiments there is no second adhesive on the third sheet part, which then functions only as a handle. Such an embodiment is particularly useful for patients with reduced gripping strength, as closing the hand around the handle makes it much easier to stretch the bandage with greater forces.

Figure 18:
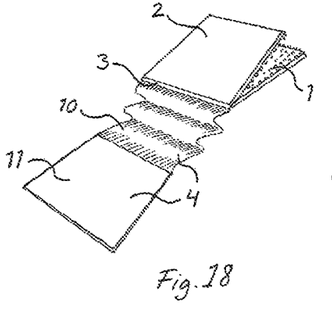

FIG. 18 shows an embodiment where the third sheet part 4 is formed by two different sections 10 and 11, where the section 10 attaches to the connection line 3. In one embodiment, the section 10 is of an elastic fabric and can be stretched around the body part so that the the section 11 of the third sheet part 4 attaches to the second sheet part 2. In yet another embodiment, both the bandage and the section 11 attaches to the first adhesive fastening layer within the jaw-like structure formed by the first sheet part 1 and the second sheet part 2.

Figure 19:
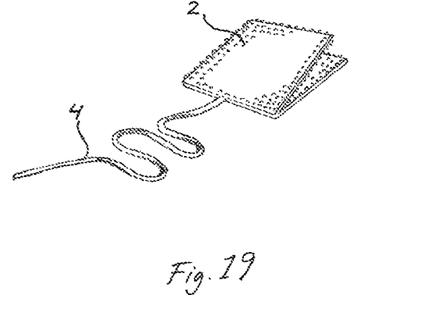

FIG. 19 shows an embodiment where the third sheet part 4 is a string that is long enough to wrap around the body part at least one turn and that can attach to the second sheet part 2, which is provided with a third adherent fastening layer. In another embodiment, there are a plurality of strings. In yet another embodiment, there is instead a narrow band or set of bands which may be provided with the second adherent fastening layer, in which case the second sheet part 2 need not be provided with a third adherent fastening layer.

Figure 20:
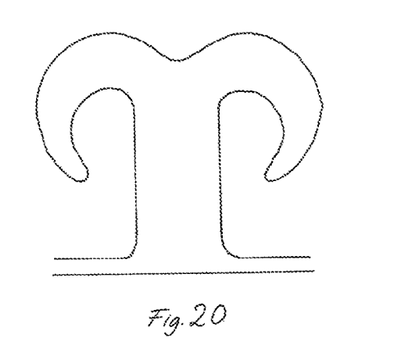
FIGS. 20-23 are enlarged side views schematically showing various hook configurations that may be used for forming the adherent fastening layers of bandage securing devices in accordance with the invention.
Figure 21:
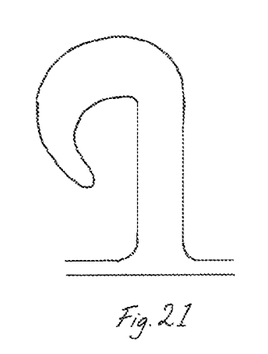
Figure 22:
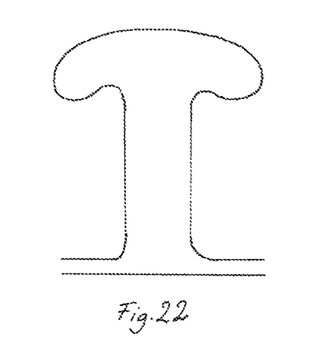
Figure 23:
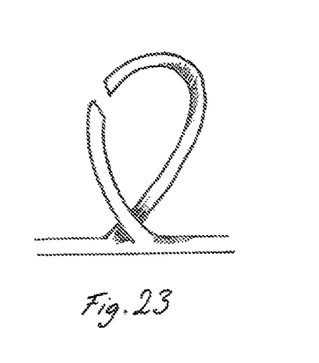

In FIGS. 20 to 23, some examples are given on the active mechanical parts on the sides that form the adhesive areas. All of these parts can attach to the bandage by hooking up into the textile structure of the bandage. In FIG. 20 there is a double hook. In FIG. 21 a single hook is illustrated. FIG. 22 shows a so called mushroom. FIGS. 20-22 are examples of molded hooks. FIG. 23 is an illustration of yet another embodiment, that for example might be from a nylon weft, consisting of a loops that has been cut open in order to create hooks. These four examples in FIGS. 20 to 23 are just illustrations of one family of possible adhering functions. The choice of size and type of hook that is preferable depend on the fabric structure of the bandage.

There are various ways to manufacture the present innovation. One preferred method for manufacturing the adhesive surfaces is injection molding of a thermoplastic material. Another method is to manufacture a hook-webbing, such as commonly used in hook and loop fasteners, to create the adhesive surfaces.

In one method the present invention is made out of two or more parts. See for example FIGS. 8 and 9. In order to assemble the adhesive parts together, one preferred embodiment is to use welding. If the adhesive parts are made in a thermoplastic material one can use ultrasonic welding. If a hook-webbing is used for the adhesive parts, incorporating a non-thermoplastic material, one can use a thermoplastic tape between the two parts, in order to weld the two parts together. In another method a seam can be used to assemble the adhesive parts.

In another method the present invention is made out of one single piece. See for example FIG. 13. This might be done by injection molding of a thermoplastic material. Other possible manufacturing processes are 3D-weaving or 3D-printing.

Yet another method includes the addition of a fabric to be laminated on the outer side of the present invention in order to make it softer and more robust.

The bandage securing device of the above-discussed embodiments works well with essentially all types of known bandages. In case adherent areas having hooks are used, the bandage preferably is a woven or knitted fabric forming corresponding loops, thereby forming a textured surface to which the hooks securely attach.

The invention has now been disclosed by reference to preferred embodiments. However, it is to be acknowledged by the skilled addressee that several further modifications are feasible. For example, many different adhesive fastening layers and combinations thereof are possible, including magnetic and chemical bonding or fusing. Further, the jaw-like structure can be realized in many different ways, some of which have been disclosed in the foregoing. However, many other alternative embodiments would be feasible to the same or similar ends.

Such and other obvious modifications must be considered to be within the scope of the present invention, as it is defined by the appended claims. It should be noted that the above-mentioned embodiments illustrate rather than limit the invention, and that those skilled in the art will be able to design many alternative embodiments without departing from the scope of the appended claims. In the claims, any reference signs placed between parentheses shall not be construed as limiting to the claim. The word "comprising" does not exclude the presence of other elements or steps than those listed in the claim. The word "a" or "an" preceding an element does not exclude the presence of a plurality of such elements.

The invention claimed is:

1. A bandage securing device comprising a first sheet part, a second sheet part, and a third sheet part, wherein said first and second sheet parts are connected to each other along a connection line extending in a width direction such that said first and second sheet parts form a monolithic integrated sheet and said connection line forms a folding line, wherein said first and second sheet parts are arranged to overlap each other, thereby forming a jaw-like structure in a longitudinal direction, and wherein said third sheet part is connected to said first and second sheet parts via said connection line and extends away from said overlap, said third sheet part comprising a textured or corrugated surface forming a gripping handle, wherein at least one of said first and second sheet parts is provided with at least one first adherent fastening layer on an internal surface facing said overlap, and wherein said bandage securing device further comprises at least one second adherent fastening layer on an external surface, not facing said overlap, said at least one first and second adherent fastening layers being arranged to detachably connect to a bandage, wherein said at least one first and second adherent fastening layers each comprise a plurality of hooks configured to engage with thread or yarn loops formed in a material of said bandage to form a detachable hook-and-loop connection, wherein at least one of said first and second sheet parts being provided with one of said at least one first and second adherent fastening layers on a surface thereof further comprises a non-adherent surface area, not being provided with said at least one first and second adherent fastening layers, wherein said non-adherent surface area is arranged on the same surface as said at least one first and second adherent fastening layers at a location on said at least one first and second sheet parts being directly adjacent to said connection line.

2. The bandage securing device of claim 1, wherein both of said first and second sheet parts have an extension in a width direction corresponding to at least a greater part of the width of said bandage.

3. The bandage securing device of claim 1, wherein said at least one second adherent fastening layer is arranged on a surface of said third sheet part.

4. The bandage securing device of claim 1, wherein said third sheet part forms a monolithically integrated part of at least one of said first and second sheet parts.

5. The bandage securing device of claim 1, wherein at least one, and preferably both, of said at least one first and second adherent fastening layers have an extension in the width direction corresponding to the width of said first and second sheet parts on which they are arranged.

6. The bandage securing device of claim 1, wherein the internal surface of each of said first and second sheet parts are provided with said at least one first adherent fastening layer.

7. The bandage securing device of claim 1, wherein at least one of said first and second sheet parts is provided with said at least one second adherent fastening layer, on an external surface thereof.

8. A bandage assembly comprising:
a bandage, formed of an elongate fabric material, made of an elastic material, woven or knitted from threads or yarns; and
a bandage securing device comprising a first sheet part, a second sheet part, and a third sheet part, wherein said first and second sheet parts are connected to each other along a connection line extending in a width direction such that said first and second sheet parts form a monolithic integrated sheet and said connection line forms a folding line, wherein said first and second sheet parts are arranged to overlap each other, thereby forming a jaw-like structure in a longitudinal direction, and wherein said third sheet part is connected to said first and second sheet parts via said connection line and extends away from said overlap, said third sheet part comprising a textured or corrugated surface forming a gripping handle, wherein at least one of said first and second sheet parts is provided with at least one first adherent fastening layer on an internal surface facing said overlap, and wherein said bandage securing device further comprises at least one second adherent fastening layer on an external surface, not facing said overlap, said at least one first and second adherent fastening layers being arranged to detachably connect directly to an outer surface of the bandage, wherein said at least one first and second adherent fastening layers each comprise a plurality of hooks configured to engage with thread or yarn loops formed by the threads or yarns of the elongate fabric material of the bandage to form a detachable hook-and-loop connection, wherein at least one of said first and second sheet parts being provided with one of said at least one first and second adherent fastening layers on a surface thereof further comprises a non-adherent surface area, not being provided with said at least one first and second adherent fastening layers, wherein said non-adherent surface area is arranged on the same surface as said at least one first and second adherent fastening layers at a location on said at least one first and second sheet parts being directly adjacent to said connection line.

9. A bandage securing device comprising a first sheet part, a second sheet part, and a third sheet part, wherein said first and second sheet parts are connected to each other along a connection line extending in a width direction such that said first and second sheet parts form a monolithic integrated sheet and said connection line forms a folding line, wherein said first and second sheet parts are arranged to overlap each other, thereby forming a jaw-like structure in a longitudinal direction, and wherein said third sheet part is connected to said first and second sheet parts via said connection line and extends away from said overlap, said third sheet part comprising a textured or corrugated surface forming a gripping handle, wherein at least one of said first and second sheet parts is provided with at least one first adherent fastening layer on an internal surface facing said overlap, and wherein said bandage securing device further comprises at least one second adherent fastening layer on an external surface, not facing said overlap, said at least one first and second adherent fastening layers being arranged to detachably connect to a bandage, wherein said at least one first and second adherent fastening layers each comprise a plurality of hooks configured to engage with thread or yarn loops formed in a material of said bandage to form a detachable hook-and-loop connection, wherein said at least one first and second sheet parts being provided with said at least one first adherent fastening layer on a surface thereof further comprises a non-adherent surface area, not being provided with said at least one first adherent fastening layer, wherein said non-adherent surface area is arranged on the same surface as said at least one first adherent fastening layer at an end of said at least one first and second sheet parts being opposite to said connection line.

10. A bandage securing device comprising a first sheet part, a second sheet part, and a third sheet part, wherein said first and second sheet parts are connected to each other along a connection line extending in a width direction such that said first and second sheet parts form a monolithic integrated sheet and said connection line forms a folding line, wherein said first and second sheet parts are arranged to overlap each other, thereby forming a jaw-like structure in a longitudinal direction, and wherein said third sheet part is connected to said first and second sheet parts via said connection line and extends away from said overlap, said third sheet part comprising a textured or corrugated surface forming a gripping handle, wherein at least one of said first and second sheet parts is provided with at least one first adherent fastening layer on an internal surface facing said overlap, and wherein said bandage securing device further comprises at least one second adherent fastening layer on an external surface, not facing said overlap, said at least one first and second adherent fastening layers being arranged to detachably connect to a bandage, wherein said at least one first and second adherent fastening layers each comprise a plurality of hooks configured to engage with thread or yarn loops formed in a material of said bandage to form a detachable hook-and-loop connection, wherein at least one of said first and second sheet parts being provided with one of said at least one first and second adherent fastening layers on a surface thereof further comprises a first non-adherent surface area, not being provided with said at least one first and second adherent fastening layers, wherein said non-adherent surface area is arranged on the same surface as said at least one first and second adherent fastening layers at an end of said at least one first and second sheet parts being opposite to said connection line, and a second non-adherent surface area, not being provided with said at least one first and second adherent fastening layers, wherein said second non-adherent surface area is arranged on the same surface as said at least one first and second adherent fastening layers at a location on said at least one first and second sheet parts being directly adjacent to said connection line.

\* \* \* \* \*